(12) United States Patent
Jordan et al.

(10) Patent No.: US 10,335,348 B2
(45) Date of Patent: Jul. 2, 2019

(54) FILLING NEEDLE FOR USE IN A TUBE LAYER FOR TRANSFERRING A FLOWABLE MEDIUM, IN PARTICULAR A PHARMACEUTICAL PRODUCT

(71) Applicant: Raumedic AG, Münchberg (DE)

(72) Inventors: Philipp Jordan, Bayreuth (DE); Steffen Hager, Helmbrechts (DE); Dominik Erhard, Kulmbach (DE); Rainer Adelung, Kiel (DE); Kristin Mess, Kronshagen (DE); Ingo Paulowicz, Kiel (DE); Fabian Schütt, Kiel (DE)

(73) Assignee: Raumedic AG, Münchberg (DE)

( * ) Notice: Subject to any disclaimer, the term of this patent is extended or adjusted under 35 U.S.C. 154(b) by 82 days.

(21) Appl. No.: 15/350,053

(22) Filed: Nov. 12, 2016

(65) Prior Publication Data

US 2017/0135904 A1    May 18, 2017

(30) Foreign Application Priority Data

Nov. 13, 2015   (DE) .......................... 10 2015 222 397

(51) Int. Cl.
*A61J 1/20*   (2006.01)
*A61M 5/00*   (2006.01)
(Continued)

(52) U.S. Cl.
CPC .............. *A61J 1/2096* (2013.01); *A61J 1/20* (2013.01); *A61L 29/00* (2013.01); *A61M 5/00* (2013.01);
(Continued)

(58) Field of Classification Search
CPC .......... A61J 1/2096; A61J 1/20; F16L 11/042; F16L 33/30; F16L 33/32; A61L 29/00;
(Continued)

(56) References Cited

U.S. PATENT DOCUMENTS 4,148,319 A * 4/1979 Kasper .................. A61M 25/00
                                                604/102.02
4,347,874 A    9/1982 Sullivan et al.
(Continued)

FOREIGN PATENT DOCUMENTS

DE   10 2006 001 178    7/2007
DE   10 2011 076 938   12/2012
(Continued)

OTHER PUBLICATIONS

Jin et al., "Joining the Un-Joinable: Adhesion Between Low Surface Energy Polymers Using Tetrapodal ZnO Linkers", Adv. Mater. 2012, 24, 5676-5680.
EP Search Report dated Jul. 21, 2017 in EP App. No. 16 19 7448.

*Primary Examiner* — Nicolas A Arnett
(74) *Attorney, Agent, or Firm* — Boyle Fredrickson S.C.

(57) ABSTRACT

A filling needle can be used in a tube set for transferring a flowable medium, in particular a pharmaceutical product. The filling needle has a needle end for temporary insertion in a filling vessel. Furthermore, the filling needle has a connector end for connecting the filling needle to a filling vessel, via which the medium can be supplied to the filling needle. An inner tube lumen of the filling needle is defined by an inner tube layer made of silicone. The result is a filling needle that can be manufactured inexpensively.

16 Claims, 5 Drawing Sheets

(51) Int. Cl.

| | |
|---|---|
| *A61M 39/00* | (2006.01) |
| *A61M 39/08* | (2006.01) |
| *A61M 39/12* | (2006.01) |
| *B65B 39/00* | (2006.01) |
| *B65B 3/04* | (2006.01) |
| *A61L 29/00* | (2006.01) |
| *F16L 11/04* | (2006.01) |
| *B65B 3/00* | (2006.01) |
| *F16L 33/30* | (2006.01) |
| *F16L 33/32* | (2006.01) |

(52) U.S. Cl.
CPC ............ *A61M 39/00* (2013.01); *A61M 39/08* (2013.01); *A61M 39/12* (2013.01); *B65B 3/04* (2013.01); *B65B 39/00* (2013.01); *F16L 11/042* (2013.01); *A61M 2209/045* (2013.01); *B65B 3/003* (2013.01); *F16L 33/30* (2013.01); *F16L 33/32* (2013.01)

(58) Field of Classification Search
CPC ........... B65B 39/00; B65B 3/04; B65B 3/003; A61M 39/12; A61M 39/08; A61M 39/00; A61M 5/00; A61M 2209/045
USPC .................................................. 604/411–414
See application file for complete search history.

(56) References Cited

U.S. PATENT DOCUMENTS

| | | | |
|---|---|---|---|
| 9,192,754 | B2 | 11/2015 | Haschke |
| 2006/0025753 | A1 | 2/2006 | Kubalak et al. |
| 2008/0228145 | A1* | 9/2008 | Watson ............ A61M 25/0612 604/164.13 |
| 2009/0053084 | A1 | 2/2009 | Klein |
| 2009/0227954 | A1 | 9/2009 | Loiterman et al. |
| 2011/0270019 | A1 | 11/2011 | Deuel et al. |
| 2012/0192987 | A1* | 8/2012 | Haschke ................ A61M 39/08 138/137 |
| 2013/0056130 | A1 | 3/2013 | Alpert et al. |
| 2013/0085413 | A1* | 4/2013 | Tsamir ................. A61B 5/0053 600/567 |
| 2014/0221970 | A1* | 8/2014 | Eaton .................. A61M 5/3202 604/506 |
| 2014/0283940 | A1* | 9/2014 | Bourgeois ............... F16L 11/04 138/137 |
| 2016/0262795 | A1* | 9/2016 | Urbanski ............. A61B 5/6848 |
| 2017/0136736 | A1* | 5/2017 | Jordan ..................... B32B 7/08 |

FOREIGN PATENT DOCUMENTS

| | | |
|---|---|---|
| DE | 10 2013 104 195 | 10/2014 |
| DE | 10 2013 010509 | 12/2014 |
| EP | 1 450 092 | 8/2004 |
| WO | 2008103484 | 8/2008 |
| WO | 2015010687 | 1/2015 |

* cited by examiner

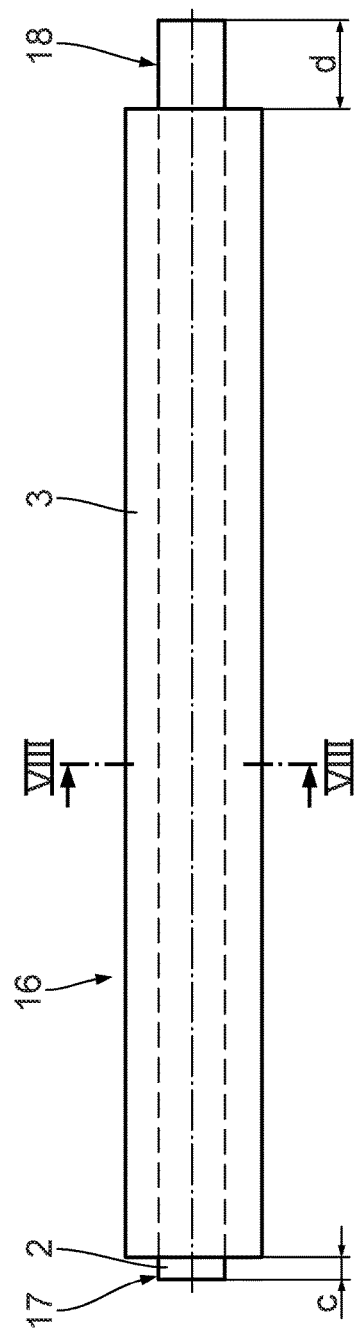
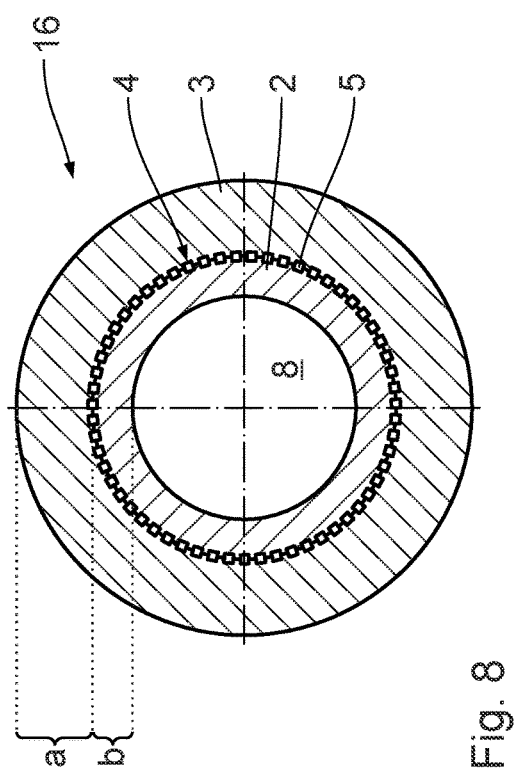
Fig. 7
Fig. 8

FILLING NEEDLE FOR USE IN A TUBE LAYER FOR TRANSFERRING A FLOWABLE MEDIUM, IN PARTICULAR A PHARMACEUTICAL PRODUCT

FIELD OF THE INVENTION

The invention relates to a filling needle for using in a tube layer for transferring a flowable medium, in particular, a pharmaceutical product.

BACKGROUND OF RELATED ART

A filling needle of this type is known from WO 2008/103 484 A2.

A silicone tube having lower permeability is known from U.S. Pat. No. 9,192,754 B2. US 2006/0025753 A1 describes a bladder catheter. US 2009/0053084 A1 describes a silicone tube section for a peristaltic pump. U.S. Pat. No. 4,347,874 describes a transfer assembly having a peristaltic pump tube and a filling needle.

SUMMARY OF THE INVENTION

An object of the present invention is to create a filling needle that can be manufactured inexpensively.

This objective is achieved according to the invention by a filling needle having the features given in Claim 1.

In accordance with the invention, it has been discovered that it is possible to create a filling needle having an inner tube layer made of silicone, defining an inner tube lumen. A filling needle of this type can be used as a disposable product, such that a complicated cleaning thereof is not necessary. The filling needle can be designed such that the flowable medium, in particular a pharmaceutical product, comes in contact exclusively with the inner silicone tube layer. An undesired contamination of the pharmaceutical product is thus prevented. The filling needle can be made on the whole exclusively of plastic.

An outer reinforcing tube layer according to Claim 2 results in an inherently stable filling needle. A complex, additional reinforcement can be omitted. The entire filling needle can be made of plastic. The reinforcing tube layer can be made of a polyolefin. The reinforcing tube layer can be made of a thermoplastic. The reinforcing tube layer can be made of a polypropylene (PP). The reinforcing tube layer can be made of polyethylene (PE), in particular low density polyethylene (LDPE). The reinforcing tube layer can also be made of polycarbonate (PC) or polysulfone (PSU).

A bonding agent according to Claim 3 prevents an undesired delamination of the filling needle or an undesired axial displacement of the inner tube layer in relation to the outer reinforcing tube layer.

Mechanical bonding bodies according to Claim 4, joining the two tube layers, have proven to be particularly suitable for generating a secure bond between the two tube layers. The bonding bodies can be tetrapods. The bonding bodies can be made of zinc oxide (ZnO). Bonding bodies of this type are fundamentally known from the scientific paper by Jin et al., Adv. Mater. 2012, 24, 5676 to 5680. The bonding bodies can have typical dimensions, in the range of 10 µm to 100 µm, in particular in the range of 10 µm to 40 µm. A bonding effect of these mechanically bonding bodies is not substantially based on adhesion, but rather on the basis of form-fitting contributions, and is based in particular on a mechanical anchoring or interlocking. As a result, a secure bond between the two layers can be obtained, without the need for secondary bonding forces, dipole-dipole forces, or hydrogen bridges. The bonding bodies can come into direct mechanical contact with the at least one silicone component on one hand, and with the at least one further polymer component on the other hand. Alternatively, it is possible for at least some, or all of the bonding bodies to be fully enclosed by one of the components of the multi-component plastic body, wherein a mechanical bonding of the two components via a form-fit contribution between the bonding bodies encased by the one component and the other component is obtained in the boundary area between the two components, due to the shape of the bonding bodies. A mechanical bonding as set forth in the application is achieved, in particular, when a form-fitting contribution, which provides a cohesion between the components of a multi-component plastic body, is obtained due to undercuts in the bonding body.

An excess of the inner tube layer at the needle end according to Claim 5 ensures that only the inner tube layer comes in contact with the flowable pharmaceutical product at the needle end. This excess can be in the range of 1 mm to 5 mm. An excess of this sort can be generated through subsequent assembly of the filling needle. An excess of this sort can also promote an advantageous dripping of the pharmaceutical product from the end of the needle.

An excess of the inner tube layer at the connector end, according to Claim 6, simplifies an assembly of the filling needle, such that the pharmaceutical product also comes exclusively in contact with only the inner silicone tube layer of the filling needle.

The advantages of a tube set according to Claim 7 correspond to those that have already been specified above in reference to the filling needle according to the invention.

A folding over of the inner tube layer according to Claim 8, or sliding inward of the inner tube layer according to Claim 9 are variations of the bonding of the inner tube layer to the connector components, which can ensure that the flowable pharmaceutical product comes exclusively in contact with the inner silicone tube layer at the connector end.

BRIEF DESCRIPTION OF THE DRAWINGS

Exemplary embodiments of the invention shall be explained in greater detail below, based on the drawings. Therein:

FIG. 7 shows a side view of a filling needle for use in a tube set for transferring a medium, in particular a flowable pharmaceutical product;

FIG. 8 shows a cross section in accordance with line VIII-VIII in FIG. 7; and

DETAILED DESCRIPTION OF THE PREFERRED EMBODIMENTS

Figure 1:
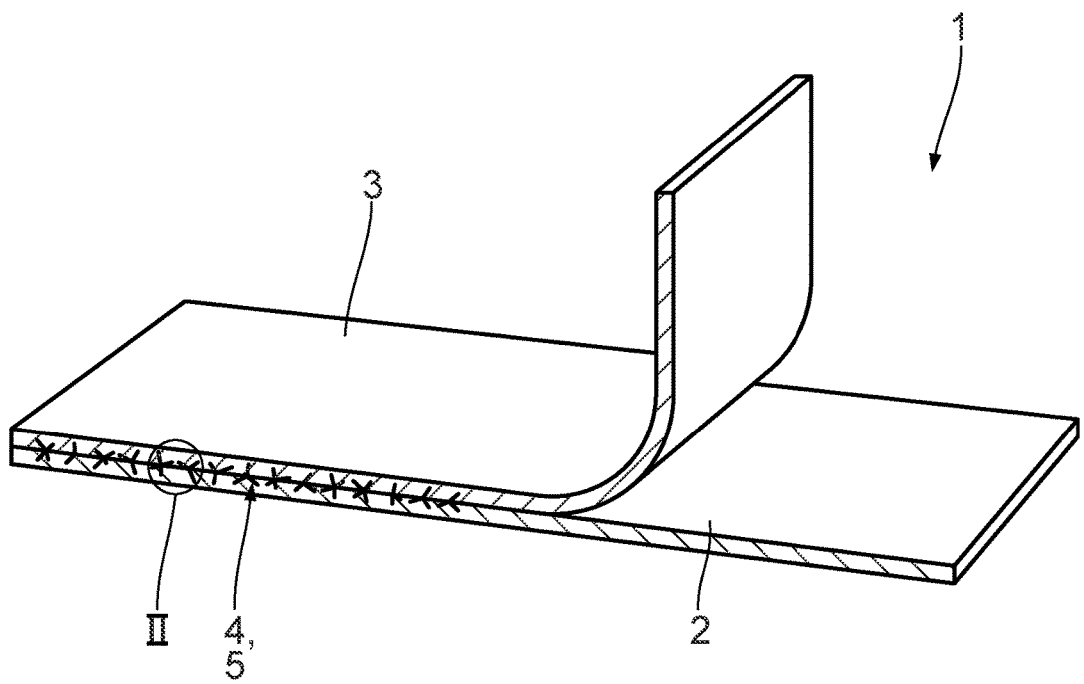
FIG. 1 shows, schematically, a multi-component plastic body having a silicone layer and a polymer layer made of a further nonpolar polymer, and a bonding agent between these two layers.

FIG. 1 shows a design of a multi-component plastic body 1, by way of example, a two-layered plastic body. The plastic body 1 has a silicone component in the form of a silicone layer 2, and a further polymer component in the form of a polymer layer 3. This further polymer layer 3 is made of a nonpolar polymer. The further polymer layer 3 is not made of silicone. The further polymer of the polymer layer 3 can be a polyethylene or polypropylene, in particular a low density polyethylene (LDPE). The further polymer component 3 can be made of a thermoplastic, in particular a thermoplastic elastomer. The further polymer can be a nonpolar polyolefin.

Examples of nonpolar polymers are polyethylene (PE), polypropylene (PP), polystyrene (PS), or polytetrafluoroethylene (PTFE). Examples of less polar polymers, which are likewise to be understood to be nonpolar polymers as set forth in this application, are copolymers made of ethylene and unsaturated esters (e.g. EVAC) or polyphenylene ether (PPE).

The multi-component plastic body 1 can be used in medical or pharmaceutical practices.

A bonding agent 4 is disposed between the silicone component 2 and the further polymer component 3. The bonding agent 4 includes the bonding bodies 5 mechanically bonding the two components 2, 3, i.e. the two layers. The bonding bodies 5 are made of zinc oxide (ZnO). The bonding bodies 5 have the shape of tetrapods. The ZnO tetrapods have a typical size in the range of 1 µm to 100 µm, in particular in the range of 10 µm to 40 µm. Free ends 6 of the bonding bodies 5 are anchored in, or interlocked to the silicone layer 2 on one side, and to the further polymer layer 3 on the other side. In this manner, a mechanical bond is obtained between the two layers 2, 3, thus between the silicone layer 2 and the further polymer layer 3. This mechanical bond has a form-fitting contribution, i.e. is not substantially based on adhesion. This does not exclude the possibility of an adhesion contribution to this bond.

Figure 2:
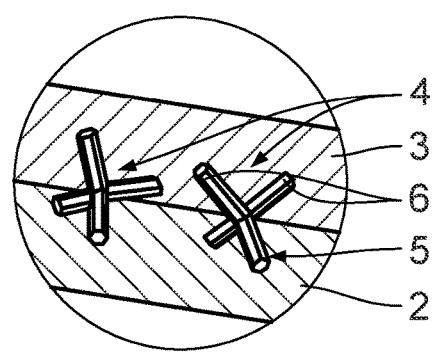
FIG. 2 shows a sectional enlargement II from FIG. 1, showing the details of the bonding agent that mechanically bonds the two layers.

In the assembly shown in the detail enlargement of FIG. 2, the bonding bodies 5 are in direct contact with the silicone layer 2 on one hand, and the further polymer layer 3 on the other hand. Alternatively, it is possible that likewise, some or all of the bonding bodies 5 are fully encased by one of the two components, i.e. either the silicone layer 2 or the further polymer layer 3, wherein a mechanical bonding between the two layers 2, 3 still results from a form-fitting contribution, generated via the shape of the bonding body, in particular via at least one undercut. By way of example, the bonding bodies 5 can be covered with the silicone material of the silicone layer 2 in the region of an end 6 or numerous ends 6, which protrude into the polymer layer 3.

To manufacture the multi-component plastic body 1, first a base component is produced, which is either the silicone component 2 or the further polymer component 3. Subsequently, the bonding agent 4 is applied to this base component 2 or 3. Lastly, a cover component, which can be either the further polymer component or the silicone component, is applied to the base component, such that the bonding agent 4 ends up lying between the silicone component 2 and the further polymer component 3.

Prior to the application of the bonding agent 4 to the base component, the bonding bodies 5 of the bonding agent 4 can be dispersed in a liquid, in particular a silicone liquid. Subsequently, the dispersed bonding bodies 5 can be applied to the base component, before the cover component is applied.

Prior to the application of the bonding agent 4, a silication of a surface of the base component facing the bonding agent 4, i.e. the silicone component 2, for example, may take place.

After applying the cover component, a heating of the raw multi-component plastic body generated in this manner can occur, by means of which, in particular, the bonding body 5 is better anchored in the layers 2, 3. After heating this raw multi-component plastic body, and subsequent cooling thereof, the finished multi-component plastic body 1 is obtained.

The silicone component 2, or the further polymer component 3 can be produced by injection molding.

Insofar as the multi-component plastic body is a multi-layered tube, as shall be explained below, the silicone and polymer components can also be produced or applied through extrusion.

For the application of a bonding agent dispersion, the respective prepared inner tube layer can be drawn through the bonding agent dispersion.

An encasing of the inner tube layer coated with the bonding agent can be obtained using a cross extruder head.

Figure 3:
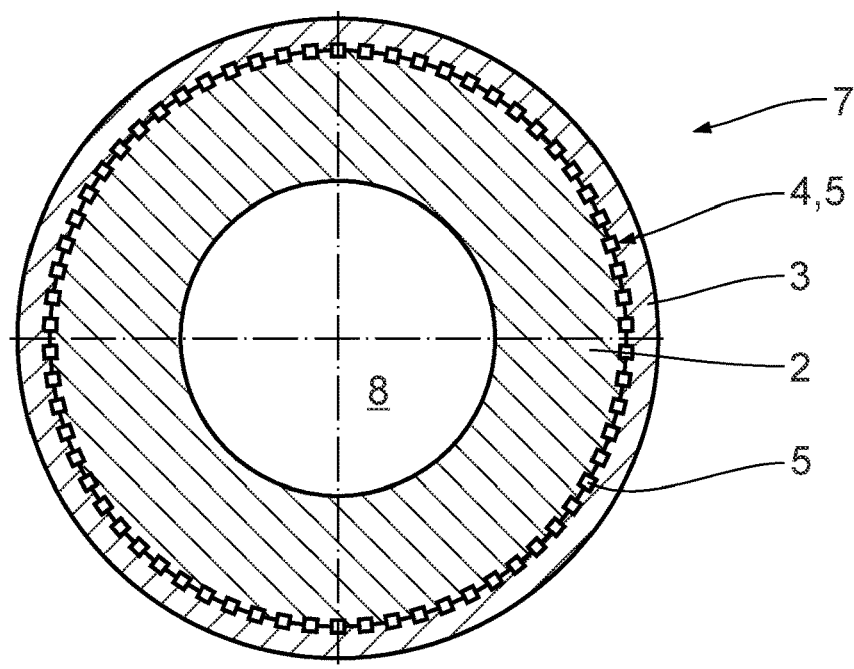
FIGS. 3 to 6 show, schematically, cross sections of a layer construction for various designs of multi-component plastic bodies, each of which are designed as multi-layered tubes.

FIG. 3 shows a multi-component plastic body designed as a multi-layered tube 7. The silicone component 2 forms a silicone tube layer thereby, and the further polymer component 3 forms a polymer tube layer. In the design according to FIG. 3, the silicone tube layer 2 is an inner tube layer of the multi-layered tube 7, which delimits a lumen 8 of the multi-layered tube 7. The silicone tube layer 3 has a hardness of Shore 60 A.

The silicone material of the silicone tube layer 3 can be a platinum cross-linked or a peroxide cross-linked silicone.

The polymer tube layer 3 of the multi-layered tube 7 made of the additional, nonpolar polymer, is an outer tube layer enclosing the silicone tube layer 2. The bonding agent 4 having the tetrapod bonding bodies 5 is disposed, in turn, between the two tube layers 2, 3 of the multi-layer tube 7. The layer thickness of the inner silicone tube layer 2 is greater than that of the outer polymer tube layer 3.

The multi-layered tube 7 can be used as a pharmaceutical transferring tube. The further polymer tube layer 3 of the multi-layered tube 7 can be colored. The outer polymer tube layer 3 can be completely opaque, or it can be colored with a dye that absorbs light in the UV range. The multi-layered tube 7 can be translucent on the whole, such that a visual checking of the lumen 8 remains possible.

The inner silicone tube layer 2 can be formed by a platinum cross-linking silicone rubber. The inner silicone tube layer 2 can have a silicated surface.

Figure 4:
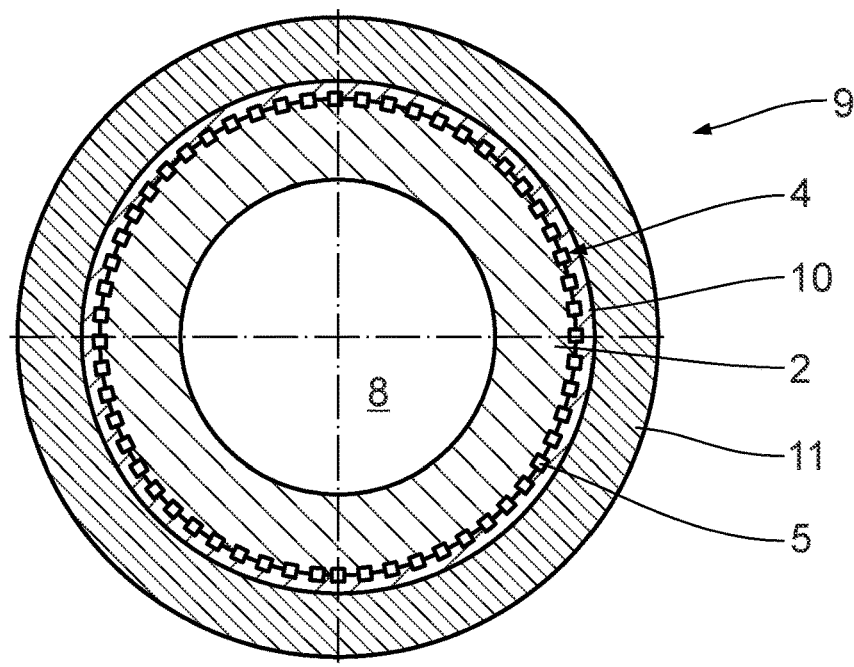

Based on FIG. 4, another design of a multi-layered tube 9 shall be explained below. Components and functions corresponding to those already explained above in reference to FIGS. 1 to 3 exhibit the same reference numerals and names, and shall not be discussed again in detail.

The multi-layered tube 9 comprises an innermost silicone layer 2, which is surrounded by an intermediate tube layer 10 made of a further polymer. The intermediate tube layer 10 represents the further polymer component of the multi-layered tube 9. The bonding agent 4 having the bonding bodies 5 is disposed between the intermediate tube layer 10 and the innermost silicone tube layer 2. The intermediate tube layer 10 is encased in an outer tube layer 11, which is designed in turn as a silicone tube layer. The outer silicone tube layer 11 is a tube layer made of UV cross-linked silicone. A thermal cross-linking step for the outer silicone tube layer 11 is no longer necessary thereby. Prior to the application of the outer silicone tube layer 11, the intermediate tube layer 10 can be functionalized in the production of the multi-layered tube 9 in order to improve the bonding of the outer silicone tube layer 11. This functionalization of the intermediate tube layer 10 can be obtained by means of a corona or plasma treatment. The intermediate tube layer 10 has a layer thickness that is thinner than the layer thicknesses of the silicone tube layers 2 and 11 of the multi-layered tube 9.

Figure 5:
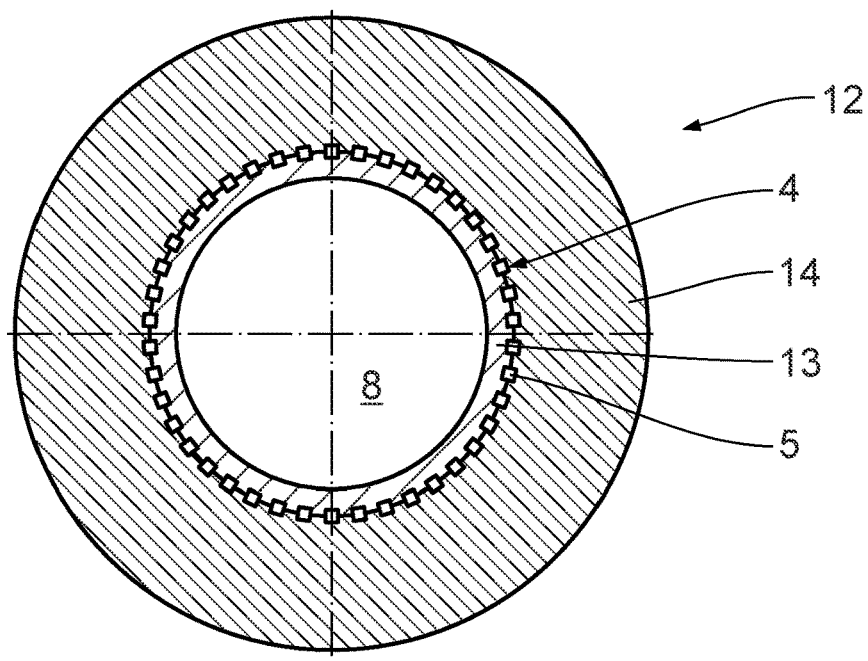

Based on FIG. 5, another design of a multi-layered tube 12 shall be explained below. Components and functions corresponding to those that have already been explained above in reference to FIGS. 1 to 4, exhibit the same reference numerals and names, and shall not be discussed again in detail.

In the multi-component tube 12, an innermost tube layer 13 is designed as the further polymer component. This is surrounded by bonding agent 4 having the bonding bodies 5, and furthermore by an outer tube layer 14, which represents the silicone component of the multi-layered tube 12. The outer silicone tube layer 14 is also a layer made of UV cross-linked silicone. The layer thickness of the inner polymer tube layer 13 is thinner than that of the outer silicone tube layer 14.

With an extrusion of the multi-layered tubes 7, 9, 12, the innermost tube layer 2, 13 is extruded first, and subsequently a bonding agent dispersion having the bonding bodies 5 is applied thereto, upon which the other tube layer 3, 14 or the intermediate tube layer 11 is applied by means of extrusion. In the three-layered tube 9 according to FIG. 4, the outer silicone tube layer 11 is subsequently applied thereto.

The multi-layered tubes 9 and 12 can be used, for example, as odor-tight rectal catheters.

Due to the fact that the polymer tube layer 10, or 13, respectively, of the multi-layered tubes 9 or 12, is thinner than the silicone tube layers 3, 11 or 14, respectively, the respective multi-layered tube 9, 12 displays good flexibility properties.

The multi-layered tubes 9 and 12 are translucent on the whole. A visual checking of the lumen 8 is possible from the exterior.

The multi-layered tubes 9 and 12 can also be used as pump tubes, in particular for a peristaltic pump.

Figure 6:
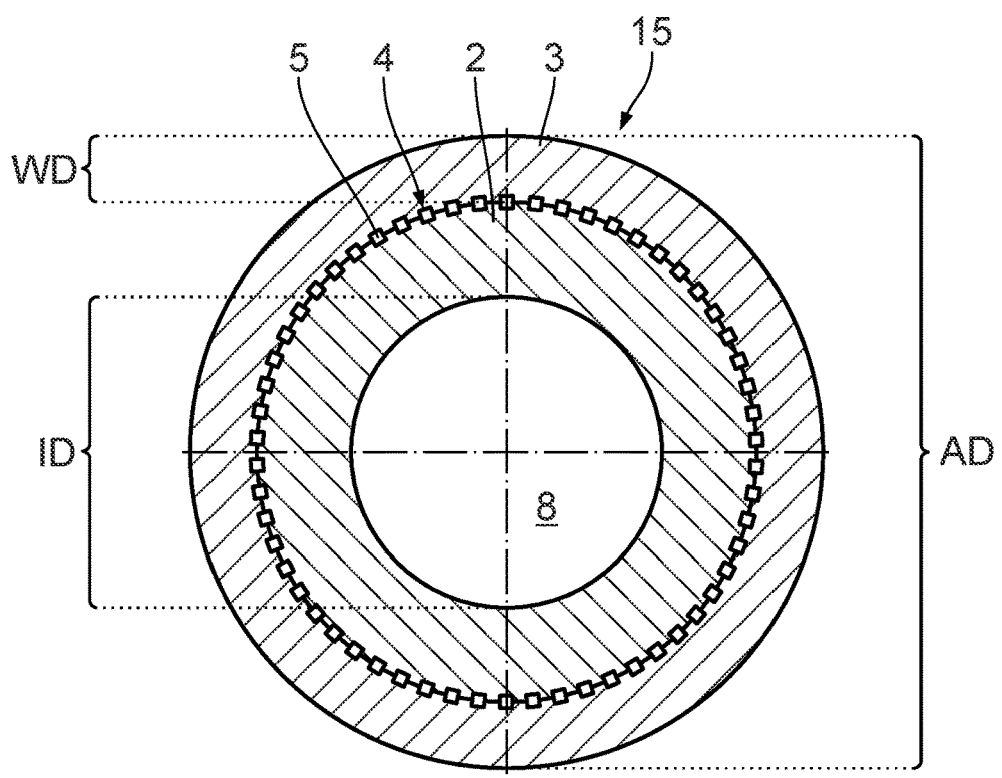

FIG. 6 shows another design of a multi-layered tube 15. Components and functions corresponding to those that have already been explained above in reference to FIGS. 1 to 5, exhibit the same reference numerals and names, and shall not be discussed again in detail.

The multi-layered tube 15 corresponds in its fundamental construction to the multi-layered tube 7 according to FIG. 3. Differences consist primarily in the diameter relationships. The multi-layered tube 15 has an outer diameter AD of 5 mm. An inner diameter ID is 1.2 mm. The wall thickness of the outer polymer tube layer WD is 0.7 mm. Accordingly, the wall thickness of the inner silicone tube layer 2 is 1.2 mm.

Another design of a multi-component plastic body in the form of a filling needle shall be explained below based on FIGS. 7 to 11. Components and functions corresponding to those that have already been explained above in reference to FIGS. 1 to 6, exhibit the same reference numerals and names, and shall not be discussed again in detail.

The filling needle 16 can be used in a tube set for transferring a flowable pharmaceutical product. A tube set of this type is fundamentally known from WO 2008/103 484 A2.

The filling needle 16 has a needle end 17, on the left in FIG. 7, for temporary insertion into a filling vessel. Furthermore, the filling needle 16 has a connector end lying opposite the needle end 17, on the right in FIG. 7, for connecting the filling needle 16 to a filling device (cf. FIG. 9), via which the pharmaceutical product can be supplied to the filling needle 16. The filling device is a component of the tube set. Neither the filling vessel nor the filling device are depicted in FIG. 7.

The filling needle 16 has an inner silicone tube layer 2 that defines an inner tube lumen 8. The tube layer sequence of the filling needle 16 corresponds in terms of its fundamental construction to that of the multi-layered tubes 7 and 15 explained above. The bonding agent 4 having the bonding bodies 5 is disposed in turn between the inner silicone tube layer 2 and the outer further polymer tube layer 3. Differences between the layer construction of the filling needle 16 and that of the multi-layered tubes 7 and 15 occur in turn in the layer thicknesses of the two tube layers 2, 3. A layer thickness a of the outer, further polymer tube layer 3 is greater than 0.7 mm. This layer thickness is greater or equal to a layer thickness b of the inner silicone tube layer 2.

The outer, further polymer tube layer 3 serves as a reinforcing tube layer. The outer tube layer 3 can be made of polypropylene.

The inner silicone tube layer 2 extends beyond the reinforcing tube layer 3 along an excess c at the needle end 17. The excess c is in the range of 1 mm to 5 mm.

The inner tube layer 2 extends beyond the outer reinforcing tube layer 3 along an excess d at the connector end 18. The excess d can be greater than the excess c.

Figure 9:
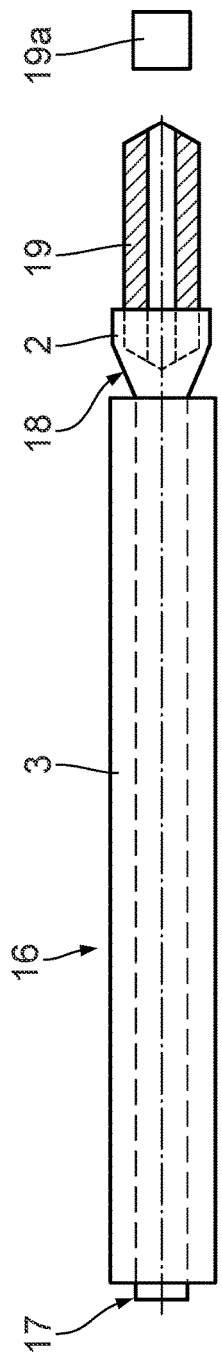
FIGS. 9 to 11 show designs of the filling needle according to FIG. 7, having various variations of a liquid-tight connection of a connector side of the filling needle with various designs of a connector component for a filling device of the tube set.
Figure 10:
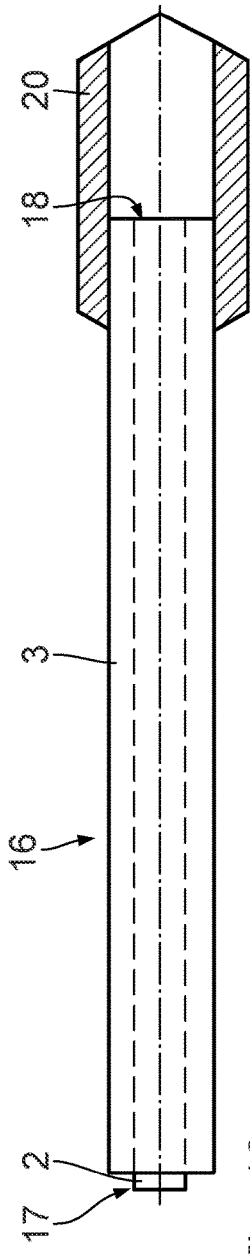
Figure 11:
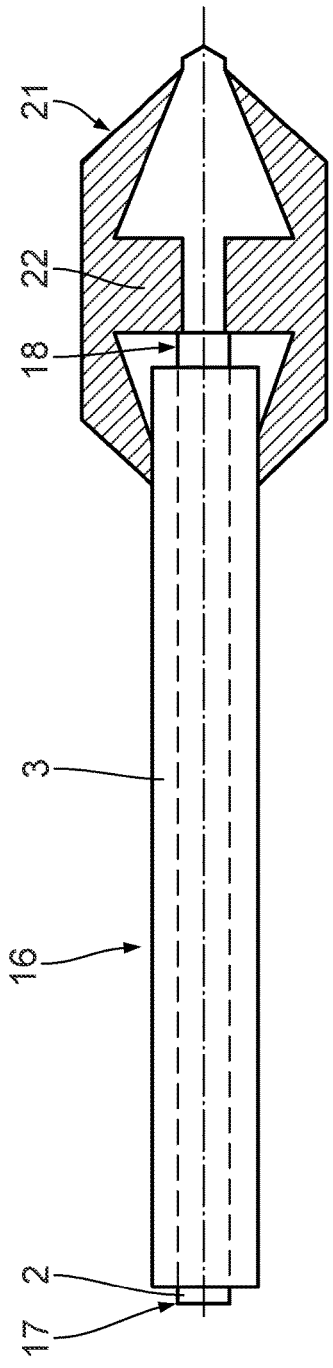

FIGS. 9 to 11 show various designs of the connector components for connecting the filling needle 16 to the filling device of the tube set. This filling device is schematically depicted in FIG. 9, indicated by the numeral 19a.

In the design according to FIG. 9, the connector component is designed as a filling tube 19, which connects the filling needle 16 to the filling device 19a of the tube set. The filling tube 19 is a silicone tube. The inner silicone tube layer 2 of the filling needle 16 is slid over the filling tube 19. The inner silicone tube layer 2 of the filling needle is thus widened in the region of the connector end 18, and placed over an outer circumference of the filling tube 19, such that the filling tube 19 is partially slid into the silicone tube layer 2 of the filling needle 16 at the connector end 18.

In the design according to FIG. 10, the connector component is likewise designed as a filling tube 20 between the filling needle 16 and the filling device of the tube set. The filling tube 20 has a significantly larger inner diameter than the filling tube 19 of the design according to FIG. 9. This inner diameter of the filling tube 20 is sized such that the filling tube 20 can be tightly slid onto the outer wall of the filling needle 16. In this case, an excess of the inner silicone tube layer 2 of the filling needle, extending over the reinforcing tube layer 3 at the connector end 18 is not necessary, as is depicted in FIG. 10.

In the design according to FIG. 11, a silicone connector 21 is used, as is known fundamentally from DE 10 2011 076 938 A1.

Alternatively to the design according to FIG. 10, the connector end 18 can also be inserted into an exposed inner silicone tube layer 2 in a filling tube designed in the manner of the filling tube 20, the diameter of which has been adapted accordingly, having a correspondingly large excess region d, which is not depicted in the drawings. An inner diameter of this variation of the filling tube 20 then corresponds to an outer diameter of the inner silicone tube layer 2.

The inner silicone tube layer 2 can adjoin an inner stop element 22 of the connector 21 in a sealing manner in the assembly according to FIG. 11, such that a liquid-tight connection of the inner silicone tube layer 2 to the connector 21 is obtained.

Through corresponding designs of the connection, which are described above in reference to FIGS. 9 to 11, it is possible to make all of the fluid channel surfaces of the tube layer from the filling vessel to the needle end 17 out of silicone or silicone rubber.

In a design of the filling needle 16 that is not depicted, a chemical bonding agent is used. In this case, bonding bodies in the manner of the bonding bodies 5 can also be omitted. Alternatively, it is possible to obtain a bonding between the two layers 2 and 3 via a combination of bonding bodies in the manner of the bonding bodies 5, and a chemical bonding component.

The invention claimed is:

1. A filling needle for use in a tube set for transferring a flowable medium, the filling needle comprising:
    a needle end for temporary insertion into a filling vessel;
    a connector end for connecting the filling needle to a filling device via which the medium can be supplied to the filling needle;
    an inner tube layer made of silicone, defining an inner tube lumen;
    an outer reinforcing tube layer made of a plastic reinforcing material, encasing the inner tube lumen; and
    a bonding agent between the inner tube layer and the reinforcing tube layer,
    wherein the bonding agent includes bonding bodies which mechanically bond the two tube layers, and
    wherein the filling needle on the whole is made entirely of plastic.

2. The filling needle according to claim 1, wherein the inner tube layer extends beyond the outer reinforcing tube layer at the needle end.

3. The filling needle according to claim 2, wherein the inner tube layer extends beyond the outer reinforcing tube layer at the connector end.

4. A tube set for transferring a flowable medium comprising:
    a filling needle according to claim 1; and a filling device for supplying the medium to the filling needle.

5. The tube set according to claim 4, wherein the inner tube layer of the filling needle is slid over a connector component with the filling device.

6. The tube set according to claim 4, wherein the inner tube layer of the filling needle is slid into a connector component with the filling device.

7. A filling needle for use in a tube set for transferring a pharmaceutical product flowable medium, the filling needle comprised of an elongate multilayer tube having (a) an inner tube layer comprised of silicone that defines an inner lumen of the tube, (b) a tube layer disposed outwardly of the inner tube layer, (c) a needle end for coupling with a filling vessel in fluid-flow communication with the inner lumen for transferring flowable medium thereto, and (d) a connector end for coupling with a filling tube in fluid-flow communication with the inner lumen through which flowable medium is introduced; and
    a bonding agent disposed between the tube layers that bonds the tube layers,
    wherein the bonding agent comprises bonding bodies that mechanically bonds the tube layers.

8. The filling needle according to claim 7, wherein the outwardly disposed tube layer is made of a tube-reinforcing material.

9. The filling needle according to claim 8, wherein the outwardly disposed tube layer is made of a plastic material that encases the inner tube lumen.

10. The filling needle according to claim 9, wherein the outwardly disposed layer is the outermost tube layer of the filling needle.

11. A filling needle for use in a tube set for transferring a pharmaceutical product flowable medium, the filling needle comprised of an elongate multilayer tube having (a) an inner tube layer comprised of silicone that defines an inner lumen of the tube, (b) a tube layer disposed outwardly of the inner tube layer, (c) a needle end for coupling with a filling vessel in fluid-flow communication with the inner lumen for transferring flowable medium thereto, (d) a connector end for coupling with a filling tube in fluid-flow communication with the inner lumen through which flowable medium is introduced, and (e) a bonding agent comprised of bonding bodies that bond the tube layers;
    wherein the filling needle on the whole is made entirely of plastic, and
    wherein the inner tube layer extends outwardly of the outwardly disposed tube layer at at least one of the needle end and the connector end.

12. The filling needle according to claim 11, wherein the inner tube layer extends outwardly of the outwardly disposed tube layer at the needle end.

13. The filling needle according to claim 11, wherein the inner tube layer extends outwardly of the outwardly disposed tube layer at the connector end.

14. The filling needle according to claim 11, wherein the inner tube layer extends outwardly of the outwardly disposed tube layer at the needle end, and wherein the inner tube layer extends outwardly of the outwardly disposed tube layer at the connector end.

15. The filling needle according to claim 14, wherein the outwardly disposed layer is made of a tube-reinforcing plastic material that encases the inner tube lumen.

16. The filling needle according to claim 15, wherein the outwardly disposed tube layer is the outermost tube layer of the filling needle.

* * * * *